United States Patent [19]

Herbert et al.

[11] Patent Number: 5,576,328
[45] Date of Patent: Nov. 19, 1996

[54] METHOD FOR THE SECONDARY PREVENTION OF ISCHEMIC EVENTS

[75] Inventors: Jean-Marc Herbert, Tournefeuille; Daniel Frehel, Toulouse; André Bernat, Cugnaux; Alain Badorc, Roquettes; Pierre Savi, Seysses; Denis Delebassée, Goyrans; Gilles Kieffer, Montpellier; Ghislain Defreyn, Eaunes; Jean-Pierre Maffrand, Portet/Garonne, all of France

[73] Assignee: Elf Sanofi, Paris, France

[21] Appl. No.: 190,332

[22] Filed: Jan. 31, 1994

[51] Int. Cl.[6] ............................................... A61K 31/44
[52] U.S. Cl. ............................................................. 514/301
[58] Field of Search ................................. 514/301, 2

[56] References Cited

U.S. PATENT DOCUMENTS 5,204,469  4/1993  Descamps et al. .................. 514/301
5,272,162  12/1993  Tjoeng et al. ....................... 514/344

OTHER PUBLICATIONS

Martindale, The Extra Pharmacopocia, 28th edition (1982) p. 735.

*Primary Examiner*—Raymond Henley, III
*Attorney, Agent, or Firm*—Jacobson, Price, Holman & Stern, PLLC

[57] ABSTRACT

The invention relates to a new method for the secondary prevention of ischemic events comprising administering to a man in need thereof a therapeutically effective amount of a compound selected from clopidogrel and its pharmaceutically acceptable acid addition salts in association with a pharmaceutically acceptable carrier.

20 Claims, No Drawings

METHOD FOR THE SECONDARY PREVENTION OF ISCHEMIC EVENTS

The invention relates to a new method for the secondary prevention of ischemic events.

More specifically, the invention pertains to the use of clopidogrel or one of its pharmaceutically acceptable acid addition salts in the secondary prevention of ischemic events.

Over the last decade, considerable interest has focused on the secondary prevention of ischemic events.

Extended histological studies of various vascular injuries have demonstrated the importance of platelets, ADP, smooth muscle cells and thrombosis in atherosclerotic cardiovascular, cerebrovascular and peripheral arterial diseases.

Although the art is replete with numerous anti-thrombotic or anti-platelet drugs, the complexity of the mechanisms responsible for secondary ischemic events largely accounts for the lack of any efficient method of treatment or prophylaxis.

As a result, large, randomized placebo-controlled clinical trials are still being performed all over the world in order to reduce the risks of prior and acute myocardial infarction, unstable and stable angina, acute reocclusion after percutaneous transluminal coronary angioplasty (PTCA), restenosis, thrombotic stroke, prior transient ischemic attack (TIA), reversible ischemic neurological deficit (RIND) and intermittent claudication occuring further to primary ischemic events.

It has now been surprisingly discovered that the administration of clopidogrel or any of its pharmaceutically acceptable acid addition salts to a patient does effectively prevent the recurrence of secondary ischemic events.

Thus, the object of the invention is to provide a method for the secondary prevention of ischemic events comprising administering to a man in need thereof a therapeutically effective amount of a compound selected from clopidogrel and its pharmaceutically acceptable acid addition salts in association with a pharmaceutically acceptable carrier.

A further object of the invention is the prevention of prior and acute myocardial infarction, unstable and stable angina, acute reocclusion after percutaneous transluminal coronary angioplasty, restenosis, thrombotic stroke, prior transient ischemic attack, reversible ischemic neurological deficit and intermittent claudication via the administration to a patient of clopidogrel or any acid addition salts thereof.

Clopidogrel is the international non-proprietary name of methyl (4)-(S)-α-(O-chlorophenyl)-6,7-dihydrothieno[3,2-c]pyridine-5-acetate having the formula

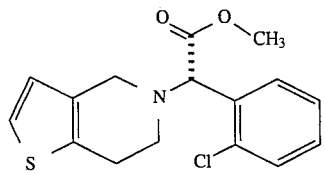

According to the invention, one preferred acid addition salt of clopidogrel is the hydrogen-sulfate.

The preparation of clopidogrel is well-known in the art.

The inventors are providing good evidence that clopidogrel, as well as the acid addition salts thereof, are efficient in the secondary prevention of ischemic events. Several pharmacological tests, the results of which are reported now, are demonstrating the efficiency of clopidogrel and its salts as a drug.

TEST 1 (ex vivo)

In this test, ADP-induced platelet aggregation was studied in male and female rats upon orally and intravenously administration of clopidogrel.

10 mg/kg of clopidogrel hydrogen-sulfate were administered to female rats either orally or intravenously. Next, at various time intervals, platelet aggregation was induced ex vivo by 2.5 μM ADP.

Upon each administration of ADP, platelet aggregation was assessed. The corresponding percentage inhibition have been reported in Table I. It should be noted that each value is the mean of the results obtained starting from a group of 6 animals. (n=6).

The Mann-Whitney-U test was used to determine the difference between vehicle- and drug-treated groups: p values have been indicated into brackets.

TABLE I

| TIME (Hours) | | 4 | 16 | 24 | 48 | 72 | 96 |
|---|---|---|---|---|---|---|---|
| % inhibition (p) | oral route | 86 (<0.001) | 80 (<0.001) | 75 (<0.001) | 55 (<0.001) | 46 (<0.001) | 25 (<0.05) |
| | intravenous route | 80 (<0.001) | 80 (<0.001) | 70 (<0.001) | 60 (<0.001) | 40 (<0.01) | 10 |

It results from Table I that by both routes (orally and intravenously), the maximum antiaggregation effect was obtained 4 hours after administration. The inhibitory activity declined thereafter but remained at significant level for at least 4 days, suggesting that clopidogrel hydrogen-sulfate irreversibly affected platelets to the remainder of their life span.

The same test was then carried out in male rats.

It appeared that the anti-aggregatory effect of clopidogrel hydrogen-sulfate was significantly higher in female rats.

Conversely, recent studies have shown that clopidogrel hydrogen-sulfate did not affect ADP-induced rat platelet aggregation in vitro, thus suggesting that in vivo metabolization was necessary for the appearing of its anti-aggregatory activity.

In this connection, the inventors have shown that the anti-aggregatory activity of clopidogrel hydrogen-sulfate disappeared after functional hepatectomy by a porto-jugular shunt, thereby supporting the fact that the activity of clopidogrel was highly dependent on hepatic metabolism.

TEST 2 (ex vivo)

A study was then performed so as to evaluate ex vivo the effect of clopidogrel hydrogen-sulfate on ADP-, collagen- and thrombin-induced platelet aggregation.

In this purpose, increasing doses of clopidogrel hydrogen-sulfate were orally administered to female rats 2 hours before induction of platelet aggregation by ADP (2.5 µM), collagen (10 µg/ml) or thrombin (0.1 IU/ml). Again, the platelet-aggregation inhibition was measured.

The obtained results have been collected in Table II.

TABLE II

| Dose (mg/kg, p.o.) | | 1.3 | 2.4 | 5 | 10 | 12.5 | 25 |
|---|---|---|---|---|---|---|---|
| % inhibition | ADP | 7 | 34 | 70 | 80 | 82 | 89 |
| | collagen | 7 | 22 | 60 | 63 | 78 | 80 |
| | thrombin | 22 | 43 | 92 | 96 | — | — |

It should be noted that each value actually corresponds to the mean response obtained from a group of 6 animals.

It ensues from the foregoing study that clopidogrel hydrogen-sulfate inhibits ADP-, collagen- or thrombin-induced platelet aggregation in a dose-dependent manner.

Moreover, it could be demonstrated that $IC_{50}$ values (doses needed to reduce platelet aggregation by 50%) in the rat were 4.0, 4.8 and 2.9 mg/kg with regard to ADP-, collagen- or thrombin-induced platelet aggregation, respectively.

TEST 3 (ex vivo)

The effect of clopidogrel hydrogen-sulfate on the tail bleeding time in rats was further assessed.

Increasing doses of clopidogrel hydrogen-sulfate were administered either by the oral route or the intravenous route. Tail transection bleeding time was measured in female rats 2 hours after administration. Results are expressed as mean-fold increase (n=6).

The Mann-Whitney-U test was used to determine the difference between vehicle- and drug-treated groups. The corresponding p values were calculated.

In Table III, the bleeding times have been plotted against the administered dose.

TABLE III

| Dose (mg/kg) | | 1.2 | 2.5 | 5 | 10 | 20 |
|---|---|---|---|---|---|---|
| Bleeding time (fold increase) (p) | oral route | 0.8 | 2.7 | 5 (<0.01) | >8 (<0.001) | >8 (<0.001) |
| | intravenous route | 1.2 | 3.1 | 7 (<0.01) | >8 (<0.001) | >8 (<0.001) |

The dose of clopidogrel hydrogen-sulfate which induced a 3-fold increase of the bleeding time was 2.5 mg/kg after either i.v. or oral administration.

In connection with this particular test, the inventors have shown that aprotinin, which is a potent protease inhibitor used in the art to reduce blood loss and blood transfusion requirements in patients undergoing open heart surgery, could be advantageously associated with clopidogrel treatment. The resulting effect proved to be dose-related.

Surprisingly, various experimental models showed that the effect of aprotinin was on no influence on the anti-aggregatory effect of clopidogrel or on its antithrombotic activity.

As a result, aprotinin might constitute a useful antagonist of the hemorrhagic risk associated with interventional therapy under treatment with clopidogrel.

TEST 4

Various thrombosis models were experimented in the rat in order to determine the influence of clopidogrel hydrogen-sulfate.

Increasing doses of clopidogrel hydrogen-sulfate were administered to female rats 2 hours before inducing thrombosis.

In the described experiments, thrombosis was respectively induced by (i) the implantation of a stainless steel wire coil in the inferior vena cava (platelet dependent experimental thrombosis model);

(ii) the insertion of a silk thread into an arterio-venous shunt placed between the carotid artery and the jugular vein;

(iii) the electrical stimulation of the carotid artery;

(iv) the induction of stasis of the inferior vena cava.

The results reported in Table IV are expressed as means % inhibition of 10 animals per group upon oral administration of clopidogrel hydrogen-sulfate.

TABLE IV

| Dose (mg/kg, p.o.) | | 1.2 | 2.5 | 5 | 10 | 20 |
|---|---|---|---|---|---|---|
| percentage inhibition | (i) model | 20 | 40 | 56 | 67 | 79 |
| | (ii) model | 25 | 51 | 73 | 86 | 90 |
| | (iii) model | 57 | 62 | 90 | 93 | — |
| | (iv) model | 12 | 80 | 86 | 83 | 88 |

Likewise, the measured $ED_{50}$ values (doses which reduce thrombus weight by 50%) have been collected in Table V together with the $ED_{50}$ values related to ADP-induced platelet aggregation.

TABLE V

| Experimental | $ED_{50}$ (mg/ml) ± SD (n = 3) | |
|---|---|---|
| Model | Oral Route | Intravenous Route |
| ADP-induced platelet aggregation | 4.0 ± 0.8 | 3.5 ± 0.5 |
| (ii) model | 2.5 ± 0.4 | 3.1 ± 1.3 |
| (i) model | 4.9 ± 1.2 | 3.3 ± 0.9 |
| (iv) model | 2.3 ± 0.75 | 1.0 ± 0.6 |
| (iii) model | 1.0 ± 0.2 | Not determined |

The above-reported results call for the following comments:

(i) When thrombosis was induced by the insertion of a wire coil into the inferior vena cava of rats, oral administration of clopidogrel hydrogen-sulfate reduced the thrombus weight in a dose-dependent manner ($ED_{50}$=4.9±0.2 mg/kg) (Table V). A nearly equal reduction was obtained after a single intravenous administration ($ED_{50}$=3.3±0.9 mg/kg) (Table V). The onset, as well as disappearance, of the antithrombotic effect closely correlated with the onset and duration of the ex vivo anti-aggregatory effect in the rat, clopidogrel hydrogen-sulfate (20 mg/kg administered orally) being able to significantly reduce thrombus formation for at least 43 hours.

(ii) On thrombosis induced in the rat on a silk thread inserted in an arteriovenous shunt, a platelet-dependent experimental thrombosis model, clopidogrel hydrogen-sulfate exhibited patent dose-dependent antithrombotic activity after oral administration (Table IV).

In the same experimental model in the rabbit, one single oral administration of clopidogrel hydrogen-sulfate (5 mg/kg, administered orally) significantly reduced thrombus formation (43% inhibition, $p<0.01$).

(iii) Electrical stimulation of the rat carotid artery resulted in acute thrombosis at the site of injury. Oral treatment with clopidogrel hydrogen-sulfate 2 hours before electrical stimulation of the carotid artery strongly reduced thrombus formation ($ED_{50}=1.0\pm0.2$ mg/kg administered orally) (Tables IV and V).

In a recent study, YAO et al. (S. K. YAO Circ. Res. 1992, 70, 39–48) confirmed the hypothesis that endogenous ADP may play an important role in mediating platelet aggregation and cyclic coronary artery blood flow variations (CFVs) in stenosed and endothelium-injured coronary arteries in an experimental canine model and showed that clopidogrel completely abolished the CFVs. CFV reinduction by epinephrine was also totally inhibited by clopidogrel. These data showed that clopidogrel may provide substantial protection against platelet aggregation leading to CFVs and experimental model of unstable angina at sites of endothelial injury and coronary artery stenosis.

(iv) When venous thrombosis was induced by ligation of the inferior vena cava of rats, clopidogrel hydrogen-sulfate administered orally 2 hours prior to thrombosis induction showed dose-dependent inhibition of thrombus formation ($ED_{50}=2.0\pm0.75$ mg/kg orally administered) (Tables IV and V).

These observations lead to the conclusion that ADP-mediated platelet activation may play a major role in the development of venous thrombosis.

Now, the inventors also report the possibility of administering clopidogrel hydrogen-sulfate in association with known thrombolytic agents such as streptokinase.

It occurs indeed that the lysis of venous thrombi by thrombolytic agents could be enhanced by clopidogrel hydrogen-sulfate.

This effect was achieved without additional prolongation of the template bleeding time observed with streptokinase alone, therefore suggesting that the concomitant use of clopidogrel hydrogen-sulfate during streptokinase therapy may facilitate clot lysis. Such observations have also been found in the dog.

These results are all the more interesting as it has recently been shown that current thrombolytic strategies have a number of important shortcomings, including the resistance to recanalization and the development of acute reocclusion.

In this respect, the use of clopidogrel hydrogen-sulfate in combination with classical thrombolytic agents could prove useful.

TEST 5

It is now recognized that the process of intimal thickening in an injured artery occuring after either percutaneous transluminal coronary angioplasty (PTCA) or in atherogenesis involves smooth muscle cell (SMC) proliferation and migration from the media to the intima.

Hence, the inventors have chosen to investigate the influence of clopidogrel hydrogen-sulfate on myointimal thickening following endothelial injury.

The carotid artherty of a rabbit was injured by air-drying, thus inducing platelet adherence to the underlying subendothelium.

Clopidogrel hydrogen-sulfate (25 mg/kg, orally administered) and the vehicle were respectively administered 2 hours before air injury and daily for 16 days to rabbits whose carotid artery was deendothelialized at day 0.

After the endothelial injury, myointimal proliferation was measured.

The corresponding data reported in Table VI are means±SD (n=9). Kruskal-Wallis test was used to determine statistical difference.

TABLE VI

| Days after air-injury | | 0 | 7 | 14 | 16 | 24 |
| --- | --- | --- | --- | --- | --- | --- |
| Intime/Media (p) | Clopidogrel hydrogen sulfate | 0 | — | — | 0.77 (<0.01) | 0.65 (<0.001) |
| | Vehicle | 0 | 0.42 | 1.16 | 1.6 | 1.6 |

These results show that clopidogrel hydrogen-sulfate can reduce myointimal thickening following endothelial injury.

Further to the above-reported pharmacological study, (double bind efficiency and safety CAPRIE study), clinical trials, which assessed the pharmacological activity, clinical and laboratory safety of clopidogrel and its salts, were performed on more than 900 healthy volunteers or patients.

Thus, the efficiency of clopidogrel and its pharmaceutically acceptable salts in the secondary prevention of ischemic events could be demonstrated.

In particular, clopidogrel or any of its acid addition salt proved useful for preventing prior and acute myocardial infarction, unstable and stable angina, acute reocclusion after percutaneous transluminal coronary angioplasty, restenosis, thrombotic stroke, prior transient ischemic attack, reversible ischemic neurological deficit and intermittent claudication.

There is no particular restriction on the route of administration. However, clopidogrel, as well as the pharmaceutically acceptable acid addition salts thereof, are preferably administered orally or intravenously, for example by intravenous bolus injection.

When administered by the oral route, clopidogrel or its salts may be formulated in conventional dosage forms, normally in admixture with a pharmaceutical carrier or diluent, for example as tablets, capsules, granules, powders or syrup. For intravenous injection, clopidogrel or its salts may be associated with a suitable pharmaceutically acceptable liquid.

The dosage may vary depending upon the age, body weight, condition of the patient and route of administration.

In case of oral administration, the daily dosage will preferably vary from 25 to 600 mg. More preferably, the active ingredient will be orally administered in a daily amount of 75 mg.

In a specific embodiment of the invention, the administration of clopidogrel or any pharmaceutically acceptable acid addition salt thereof is concomitant to the administration of aprotinin.

We claim:

1. A method for preventing the occurrence of a secondary ischemic event comprising administering to a patient who has suffered a primary ischemic event a therapeutically effective amount of a compound selected from clopidogrel and a pharmaceutically acceptable acid addition salt thereof, together with a pharmaceutically acceptable carrier.

2. The method according to claim 1, wherein the primary and/or secondary ischemic event is a myocardial infarction.

3. The method according to claim 1, wherein the primary and/or secondary ischemic event is unstable or stable angina.

4. The method according to claim 1, wherein the primary and/or secondary ischemic event is acute reocclusion after percutaneous transluminal coronary angioplasty.

5. The method according to claim 1, wherein the primary and/or secondary ischemic event is restenosis.

6. The method according to claim 1, wherein the primary and/or secondary ischemic event is thrombotic stroke.

7. The method according to claim 1, wherein the primary and/or secondary ischemic event is a transient ischemic attack.

8. The method according to claim 1, wherein the primary and/or secondary ischemic event is reversible ischemic neurological deficit.

9. The method according to claim 1, wherein the primary or secondary ischemic event is intermittent claudication.

10. A method according to claim 1, in which said acid addition salt is the hydrogen-sulfate.

11. A method according to claim 1, wherein the route of administration of the compound is either the oral route or the intravenous route.

12. A method according to claim 1, wherein the compound is orally administered in a daily amount varying from 25 to 600 mg.

13. A method according to claim 1, wherein the compound is orally administered in a daily amount of 75 mg.

14. A method according to claim 1, wherein the administration of the compound is concomitant to the administration of aprotinin.

15. The method according to claim 1, wherein said compound is selected from clopidogrel and clopidogrel hydrogen-sulfate said compound being administered in combination with a thrombolytic agent.

16. The method according to claim 15, wherein the thrombolytic agent is streptokinase.

17. The method of claim 15, wherein the compound is clopidogrel hydrogen-sulfate.

18. The method of claim 14, wherein the compound is clopidogrel hydrogen-sulfate.

19. The method of claim 1, wherein the compound is clopidogrel hydrogen-sulfate.

20. A method of preventing ischemia-induced secondary ischemia comprising administering to a patient who has suffered an ischemic event a therapeutically effective amount of a compound selected from clopidogrel and a pharmaceutically acceptable acid addition salt thereof, together with a pharmaceutically acceptable carrier.

* * * * *

Disclaimer 5,576,328 — Jean-Marc Herbert, Tournefeuille; Daniel Frehel, Toulouse; Andre Bernat, Cugnaux; Alain Badorc, Roquettes; Pierre Savi, Seysses; Denis Delebassee, Goyrans; Gilles Kieffer, Montpellier; Ghislain Defreyn, Eaunes; Jean-Pierre Maffrand, Portet/Garonne, all of France. METHOD FOR THE SECONDARY PREVENTION OF ISCHEMIC EVENTS. Patent dated November 19, 1996. Disclaimer filed August 23, 2004, by the assignee, Sanofi-Synthelabo.

Hereby disclaims the entire remaining term of said patent.

*(Official Gazette, November 2, 2004)*